United States Patent [19]

Morrow et al.

[11] Patent Number: 5,381,002

[45] Date of Patent: Jan. 10, 1995

[54] FLUORESCENCE METHOD OF QUANTIFYING HYDROCARBONS, INCLUDING CRUDE OIL, DISPERSED IN WATER

[75] Inventors: Lawrence R. Morrow, Richmond; Wilson K. Martir, Houston; Hossein Aghazeynali, Sugar Land, all of Tex.

[73] Assignee: Texaco Inc., White Plains, N.Y.

[21] Appl. No.: 51,710

[22] Filed: Apr. 23, 1993

Related U.S. Application Data

[63] Continuation-in-part of Ser. No. 982,337, Nov. 27, 1992, abandoned.

[51] Int. Cl.[6] ............................................. G01N 21/64
[52] U.S. Cl. ................................. 250/301; 250/461.1
[58] Field of Search ............................. 250/301, 461.1

[56] References Cited

U.S. PATENT DOCUMENTS

| | | | |
|---|---|---|---|
| 2,367,664 | 1/1945 | Campbell et al. | 250/255 |
| 2,403,631 | 7/1946 | Brown | 250/255 |
| 2,591,737 | 4/1952 | Souther, Jr. | 250/255 |
| 3,205,353 | 9/1965 | Bray | 250/43.5 |
| 3,254,959 | 6/1966 | Fallgatter et al. | 250/255 |
| 3,842,270 | 10/1974 | Gregory et al. | 250/301 |
| 3,887,331 | 6/1975 | Baldwin | 436/31 |
| 4,031,398 | 6/1977 | Callis et al. | 250/458.1 |
| 4,248,599 | 2/1981 | Mommessin et al. | 23/230 HC |
| 4,446,370 | 5/1984 | Gergely | 250/301 |
| 4,609,821 | 9/1986 | Summers | 250/255 |
| 4,696,903 | 9/1987 | Owen | 436/28 |
| 4,814,614 | 3/1989 | Tsui | 250/301 |
| 4,858,465 | 8/1989 | Molina | 73/104 |
| 4,977,319 | 12/1990 | Supernaw | 250/255 |
| 4,990,773 | 2/1991 | Supernaw | 250/255 |

FOREIGN PATENT DOCUMENTS

| | | | |
|---|---|---|---|
| 3-226655 | 10/1991 | Japan | 250/301 |
| 85/02015 | 5/1985 | WIPO | 250/255 |

OTHER PUBLICATIONS

David Green, Blair Humphrey and Brian Fowler, "The Use of Flow-Through Fluorometry for Tracking Dispersed Oil." 8th Biennial API, EPA and U.S. Coast Guard Oil Spill Conference (1983) pp. 473–475.

James G. Speight and Speros E. Moschopedis, "On the Molecular Nature of Petroleum Asphaltenes." in: James W. Bunger and Norman C. Li, editors, *Chemistry of Asphaltenes* (Washington, D.C., American Chemical Society, 1981) pp. 1–15.

David S. Page, Judith C. Foster, Janet R. Hotham. Donna Vallas, Edward S. Gilfillan, Sherry A. Hanson and Ray P. Gerber, "Tidal Area Dispersant Project: Fate of Dispersed and Undispersed Oil in Two Nearshore Test Spills." in: Tom E. Allen, editor, *Oil Spill Chemical Dispersants: Research, Experience, and Recommendations*, STP 840, (Philadelphia, American Society for Testing and Materials, 1984) pp. 280–298.

Skoog, Douglas A., *Principles of Instrumental Analysis*, Sanders College Publishing, Philadelphia (3rd ed. 1985), pp. 225–240.

Hemphill, W. R. et al., "Laboratory Analysis and Airborne Detection of Materials Stimulated to Luminesce by the Son", *Journal of Luminescence*, vol. 31 and 32, pp. 724–726, North-Holland, Amsterdam (1984).

Chisholm, B. R., Eldering, H. G., Giering, L. P., and Hornig, A. W., "Total Luminescence Contour Spectra of Six Topped Crude Oils", BETC/RI-76/16, a paper prepared for ERDA for the Bartlesville Energy Research Center in Bartlesville, Okla., Nov. 1976.

(List continued on next page.)

*Primary Examiner*—Constantine Hannaher
*Attorney, Agent, or Firm*—James L. Bailey; Kenneth R. Priem; Harold J. Delhommer

[57] ABSTRACT

A method to determine the amount of oil, including dispersed oil, in water at low levels wherein a surfactant is first mixed with water which may contain dispersed oil, the surfactant comprising a non-aromatic surfactant able to solubilize into water the particular oil being tested for, and comparing the emission fluorescence of the surfactant/water mixture to previous correlations drawn between known amounts of oil in water and their emission fluorescence under similar conditions.

9 Claims, No Drawings

OTHER PUBLICATIONS

Brownrigg, J. T. and Hornig, A. W., "Low Temperture Total Luminescence Contour Spectra of Six Topped Crude Oils and their Vacuum Distillate and Residuum Fractions", BETC/RI-78/13, a paper prepared for DOE for the Bartlesville Energy Technology Center, Bartlesville, Okla., Jul. 1978.

Gordon, Arnold J. and Ford, Richard A., *The Chemist's Companion*, John Wiley & Sons, NY, 1972, pp. 167 and 168.

A monograph by Turner Design entitled "Fluorometric Facts-Oil in the Environment" of unknown date.

FLUORESCENCE METHOD OF QUANTIFYING HYDROCARBONS, INCLUDING CRUDE OIL, DISPERSED IN WATER

BACKGROUND OF THE INVENTION

This is a continuation-in-part of U.S. patent application Ser. No. 07/982,337, filed Nov. 27, 1992, now abandoned.

This invention is related to techniques for determining the presence of hydrocarbons in water. Particularly, the invention offers a fluorescent method for determining the presence and amount of hydrocarbon in water, including crude oil dispersed in water.

After produced water from an oil well has been treated to remove most of the free oil, small quantities of free oil that are dispersed in the water can remain, usually as small oil droplets. Current commercial methods cannot easily and accurately detect the presence and amount of this dispersed hydrocarbon in water when it is present in low quantities of 1 ppm or greater, even though such amounts may cause an oil sheen to appear upon bodies of water.

Produced water may contain another category of oil called "soluble oil." This is hydrocarbon which can be dissolved in water due to its nature, such as benzene, which has a slight solubility in water. Produced water may contain water soluble organics (WSO). WSO compounds are soluble due to their functional groups, such as hydroxyl and carboxylic moieties. WSO compounds are broadly classified as naphthenic acids.

Unlike dispersed oil, soluble oil can be measured with commercial methods. It is well-known that WSO compounds and soluble oil are fluorescent materials which can be measured using a fluorometer in a produced water stream. Manufacturers of fluorescent detecting instruments describe the ability to measure WSO compounds and dissolved oil-in-water within their product literature. However, a method of measuring dispersed oil in water directly has not been described in the literature. Dispersed oil is not the small water soluble fraction of oil in water, and must be extracted into a solvent to be measured by current fluorescent and infrared techniques.

Molecular fluorescence is discussed in general in Skoog, Douglas, *Principles of Instrumental Analysis*, Sanders College Publishing, Philadelphia (3rd ed. 1985), pp. 225–240. The reference indicates that the greatest fluorescence behavior occurs with compounds containing aromatic functional groups and offers a table which indicates the UV fluorescence wavelengths associated with numerous benzene derivatives in ethanol solution. Several analytical profiles of hydrocarbons are disclosed wherein fluorescence intensity is plotted over multiple excitation and emission wavelengths.

Fluorescence has been used as a logging technique for detecting oil and drill cuttings for decades. Until recently, the method used to determine the presence of oil in drill cuttings was a crude method, wherein an operator shined a broad spectrum ultraviolet light source on the cuttings in the hope of seeing substantial fluorescence to indicate the presence of oil.

The emission fluorescence of crude oil samples has been studied and recorded over various wavelengths, including ultraviolet wavelengths below 400 nm. Studies which have taken place at the Bartlesville Energy Technology Center have been basically "fingerprint" studies wherein the emission fluorescence of various types of crude oils has been recorded at different excitation wavelengths. This Department of Energy research was a spin-off from earlier efforts by the Bureau of Mines to try to identify crude oil by emission fluorescence for purposes of pollution control. Please see Chisholm, B. R., Eldering, H. G., Giering, L. P., and Hornig, A. W., Total Luminescence Contour Spectra of Six Topped Crude Oils, BETC/RI-76/16, a paper prepared for ERDA for the Bartlesville Energy Research Center in Bartlesville, Okla., November 1976; and Brownrigg, J. T. and Hornig, A. W., Low Temperature Total Luminescence Contour Spectra of Six Topped Crude Oils and their Vacuum Distillate and Residuum Fractions, BETC/RI-78/13, a paper prepared for DOE for the Bartlesville Energy Technology Center, Bartlesville, Okla., July 1978. Similar, non-published fingerprinting work of crude oils by total luminescence spectra has also been performed in unpublished work at Texas A. & M. University.

There are three recently developed processes which employ fluorescent measurement to test for the presence of hydrocarbons within drill cuttings. One process, disclosed in U.S. Pat. No. 4,609,821, is applicable only to oil base mud drill cuttings. The cuttings are excited with a wide range of UV wavelengths and the emitted radiation is recorded over a wide range of wavelengths to produce an analytical chemical profile. This profile of intensity over multiple wavelengths of excitation and emission radiation is compared with previous profiles to determine the presence of hydrocarbons not associated with the oil base mud.

U.S. Pat. No. 4,977,319 discloses a method of determining the presence and concentration of hydrocarbons in a formation. It involves the steps of solvating a sample in a known volume of solvent and measuring the emission fluorescence below about 400 nm of the excited sample and comparing the emission fluorescence to previous correlations drawn between known hydrocarbon contents of samples and the emission fluorescence of the known samples in the solvent.

A similar method is disclosed in U. S. Pat. No. 4,990,773 for determining the producibility of any hydrocarbons present in the formation. In this method, two solvents are employed, one of which will solvate all petroleum fractions including asphaltenes, and a second solvent which will solvate most crude fractions without substantially solvating asphaltenes. An indication of producibility or viscosity can be obtained by comparing the ratio of the emission fluorescence of the two solvated samples with previous correlations made with samples of known producibility.

The use of a fluorometer to track crude oil in an oil spill that has been treated with a dispersant is described in D. Green et al., "The Use of Flow-Through Fluorometry for Tracking a Dispersed Oil," *8th Biennial API, EPA and U S. Coast Guard Oil Spill Conference*, 1983, pp. 473–5. The article describes the use of a dispersant sold under the trademark Corexit 9527 by Exxon Chemical Company, the only Coast Guard accepted dispersant for marine oil spills. Although this dispersant falls under the broad class of nonionic surfactants, it is composed of an ether solvent and fatty acid esters and is discussed herein in Example 4. The article states that the fluorometer was employed for detecting "soluble oil" and not dispersed oil. The title contains the phrase "dispersed oil" because crude oil was treated with a dispersant.

The same Exxon dispersant Corexit 9527 is also discussed in the context of monitoring "dispersed oil" in water by fluorescence in the article D. S. Page et al., "Tidal Area Dispersant Project: Fate of Dispersed and Undispersed Oil in Two Nearshore Test Spills," *Oil Spill Chemical Dispersants: Research, Experience and Recommendations*, 1984, ASTM Special Technical Publication No. 840. Measuring oil spills in fresh water or seawater is relatively easy to do because there is no background fluorescence in the water allowing the easy detection of soluble oil. When measuring dispersed oil in produced water, there is always a baseline fluorescence due to soluble oil. The produced water is saturated with soluble oil and additional dispersed oil cannot be detected.

A monograph by Turner Design entitled "Fluorometric Facts—Oil In The Environment" of unknown date discusses previous studies performed using fluorescence to determine the presence of oil in the environment. The article stresses that only a small amount of dissolved aromatic oil is necessary for a fluorometer to detect the oil in water and notes that emulsified crude oil from Prudhoe Bay was detected in low concentrations. However, crude oil will exist as an emulsion with water until treated with chemicals, and some dissolved aromatic hydrocarbons will be present in the water of the emulsion. The fluorometer was detecting this dissolved component as noted in the monograph.

Several studies noted in the Journal of Physical Chemistry deal with microemulsions which are single phase, clear solutions with fixed proportions of hydrocarbon, water, surfactant and alcohol. If the balance changes, the microemulsions break up. These studies do not deal with crude oil, but alkanes such as dodecane as the hydrocarbon portion of the microemulsion. An organic molecule called pyrene was used as a probe. The size of the microemulsion was studied by the changes in the fluorescent emissions spectrum of pyrene. Alkanes were added in different amounts to change the size. Please see P. Lianos, et al. "Fluorescent—Probe Study of Oil-In-Water Microemulsions," Journal of Physical Chemistry, Vol. 88, 1984, pp. 819-822 and two related prior studies cited therein (Vol. 86, 1982, pp. 1019 and 4809). For a study dealing with the nature of the aqueous core of inverted micelles, please see M. Wong, et al., "Fluorescent Probing of Inverted Micelles," Journal of the American Chemical Society, Vol. 98, 1976, pp. 2392.

Other microemulsion fluorescent studies can be found at S. Atik, "Photochemical Studies of An Oleate in Water Microemulsion," Journal of the American Chemical Society, Vol 103, No. 25, December 1981, p. 7403-6 and M. Aoudia, "Light Scattering of Fluorescent Studies of O/W Microemulsion: The Sodium 4-Dodecylbenzenesulfonate-butanol-water-NACL-Octane System," Journal of Colloid and Interface Science, Vol. 144, No. 2, July 1991, p. 353-62.

SUMMARY OF THE INVENTION

The invention is a method of quantifying the amount of hydrocarbon, including crude oil, dispersed in water at low levels. A surfactant is first mixed with water which may contain dispersed hydrocarbon, said surfactant comprising a non-aromatic, surfactant, preferably a nonionic, alkoxylated surfactant able to solubilize into water the particular hydrocarbon being tested for. Second, the mixture of surfactant and water is excited in a fluorometer at an excitation wavelength at which most petroleum compounds fluoresce. Third, the amount of the hydrocarbon in water is determined by comparing the emission fluorescence of the mixture to previous correlations. The previous correlations are drawn between known amounts of hydrocarbon in water and their emission fluorescence under similar conditions.

The invention method may be employed in a continuous on-line monitoring system or in a batch mode. One option to reduce surfactant monitoring costs is to monitor for a selected period of time when an upset occurs.

DETAILED DESCRIPTION

Fluorescence is a phenomena wherein certain compounds, containing molecular arrangements generally referred to as chromophores, emit fluorescent radiation when excited by incoming light of certain wavelengths. The chromophores contained in compounds such as the asphaltenic, aromatic and resin fractions of crude, fluoresce in the UV portion of the electromagnetic spectrum when bombarded with radiation of the proper excitation wavelength.

The chromophores, which cause fluorescence, are located in much greater numbers in viscous crude oils. As noted later, very light crude oils are difficult to detect with fluorescent measurements, although certain adjustments can be made.

There are several methods for determining the amount of dispersed and soluble crude oil in water. They involve indirect techniques, such as measurements of turbidity or extraction of the produced water stream with a solvent followed by measurement with a spectrophotometer or other sensing device. Unlike the invention method, all of these existing methods suffer from the disadvantage of having to cool the produced water prior to using the method, making them more difficult to use in most produced water situations, especially in steamfloods. All these methods are time consuming and may only give total oil and not free oil. A total organic carbon instrument can measure total dissolved oil and WSO compounds directly in the water, but free oil can plug or deposit onto the lines leading into the instrument.

There are two EPA designated methods, one of which is a infrared method using freon to extract oil from produced water, designated the 413.2 method after the applicable regulation. The other method is the EPA 413.1 laboratory method wherein water is extracted with a fluorinated hydrocarbon such as Freon ®, separated, and the Freon ® evaporated off. Both methods, which involve periodic sampling, are required by the EPA for offshore use prior to disposal of produced water. The freon methods give the total amount of free oil, soluble oil and some WSO compounds. But both EPA freon methods suffers from three disadvantages. They leave Freon ® behind in the sample water, which creates a waste subject to toxic waste disposal regulations. Second, the solvent required for numerous batch tests is expensive. Third, these methods require multiple, labor intensive steps of adding solvent, shaking, separating and detecting.

A fourth method of determining oil-in-water is referred to as the "Hach oil-in-water method," a description of which can be found in the *Water Analysis Handbook*, published by the Hach Company of Loveland, Colo. This colorimetric extraction method compares the difference in color of a 1,1,1-trichloroethane solvent used to extract a produced water sample against a predetermined scale. An instrument is sold by the Hach Company to perform this comparison. The method is discussed for oil concentrations of 0 to 85 ppm on pages 427-29 of the *Water Analysis Handbook*.

We were faced with the problem of trying to develop an on-line monitoring system which would trigger an alarm whenever the oil content in our treated discharged water exceeded a certain level. Although our induced gas floatation units normally removed sufficient oil so that our discharge was problem free, occasionally an upset in the water treating system would occur, causing the release of water containing more than the desired amount of oil. Monitoring with turbidity meters did not prove satisfactory due to an abnormally large number of false alarms caused by assorted biomass or sand carried in the treated water, which would trigger the turbidity meter alarm.

We felt that a continuous, on-line monitoring system could be developed based around fluorescent excitation of free hydrocarbon in water. To our surprise, we discovered that a fluorometer will not accurately measure free oil in water when that free oil is in a dispersed state. We unexpectedly discovered that non-aromatic surfactants, especially nonionic, ethoxylated linear alcohols having about 8 to about 20 carbon atoms in an alkyl chain were able to almost instantly transform the dispersed oil, into a state where its emission fluorescence could be measured by a fluorometer.

The invention method comprises a multistep method of mixing a surfactant with water which may contain dispersed oil, exciting the mixture of surfactant and oil in a fluorometer at an excitation wavelength at which most petroleum compounds fluoresce, and determining the amount of oil, including dispersed oil, in the water by comparing the emission fluorescence of the mixture to previous correlations. The surfactant comprises a nonionic, non-aromatic, alkoxylated surfactant able to solubilize into water the particular oil being tested for. The previous correlations are drawn between known amounts of oil-in-water and their emission fluorescence under similar conditions.

The surfactant used as an additive in the invention method should have several attributes. First, it must be non-aromatic. Although some aromatic surfactants may work with the invention method, they introduce the unneeded complication of having to subtract out the fluorescence effect of the aromatic surfactant from the overall amount of emitted radiation, which in some cases may overwhelm the emission radiation due to the hydrocarbon.

The surfactant should preferably be nonionic and alkoxylated, for we have found that this category seems to work better with the invention detection method. The surfactant should have a relatively low foaming capability because air bubbles will interfere with fluorescent measurements. The surfactant should also be reasonably stable at elevated temperatures if it will be used to monitor treated water in a steamflood, where the temperature of the produced water can reach 80° C. or more. The surfactant must also be able to solubilize the particular hydrocarbon into water. This should only be a problem if the particular crude oil related to the produced water is a viscous crude containing a number of asphaltenic fractions. It may be necessary to employ a different surfactant for certain viscous crudes, although the surfactants preferred herein worked well with Kern River crude having a 17° API gravity.

The preferred surfactant additive is a linear alcohol having about 8 to about 20 carbon atoms in an alkyl chain and about 2 to about 14 groups of ethylene oxide. Most preferred is a linear alcohol surfactant having about 10 to about 15 carbon atoms in an alkyl chain and about 3 to about 10 groups of ethylene oxide, such as the ethoxylated nonionics sold by Texaco Chemical Company under the trademarks Surfonic L24-3, L24-7, and L24-9. The surfactant is preferably added in the range of about 0.1% to about 3% by weight of the mixture, more preferably about 0.3% to about 0.7% by weight.

Optimum excitation and emission wavelengths are in the region around 400 nm. Below 400 nm is the ultraviolet region where the human eye has no response. Preferably, the samples are excited at a wavelength or narrow range of wavelengths between about 200 to about 400 nm. Preferably, emission radiation should be measured in the wavelength range of about 250 to about 600 nm.

Since there is a strong linear relationship between fluorescent readings according to the invention method and hydrocarbon concentration, the fluorescent reading is directly proportional to the concentration of hydrocarbon in the water sample, including dispersed hydrocarbon. By establishing correlations between prior fluorescent readings and known concentrations of the same crude oil, the fluorescent reading of a water with an unknown crude oil content can be directly transformed into a known oil content. Thus, by examining a side stream of treated water with a fluorometer and surfactant additive according to the invention method, an alarm can be triggered whenever oil content, including dispersed oil, goes above a selected level.

Preferably, a single fluorescence intensity measurement is obtained for each reading or sample, rather than multiple intensity measurements at multiple excitation wavelengths. However, since different crude components, different crude oils, different chemical additives in treated water, and minerals fluoresce at different wavelengths, it may be desirable to obtain multiple intensity measurements at different wavelengths in order to decrease the influence of a particular component in the oil sample being measured. For example, an emulsion breaker employed upstream of a detector according to the invention method may fluoresce strongly around 250 nm and not fluoresce strongly at about 300 nm. To substantially eliminate the effect of the emulsion breaker, it may be desirable to change the excitation or emission wavelength from around 250 nm to about 300-310 nm or about 320-330 nm. Such changes can be made by adjusting or changing the source lamp, the excitation filter, or the emission filter of the fluorometer.

In actual practice, water treating chemicals are unlikely to substantially increase or decrease fluorescent readings. Because of cost and efficacy, most water treating chemicals are used in quantities of 1-3 ppm. Example 3 showed little fluorescence effect from several common water treating chemicals when used at quantities as high as 50 ppm. However, one should not assume that any treating chemical or other additive will have little effect upon the fluorescent measurements. It is a simple matter to perform comparison tests and (1) adjust the fluorescent readings to take any added fluorescence of a treating chemical into account, or (2) change excitation or emission wavelengths to substantially eliminate any effect of treating chemicals on fluorescent readings, or (3) both of the above.

Solid contaminants will not usually interfere with the invention method since the invention method will normally be practiced at a location where most solid contaminants have already been removed from the produced water. A preferred location is downstream of the water treatment system where few solids would be encountered.

If solid contaminants exist to a substantial degree in the water to be measured, they may interfere with the fluorescent measurement of the invention method. The predominant method of interference would be a solid precipitate which would block the passage of light through the fluorometer cell, yielding a fluorescent reading not indicative of the oil content in the water. Solid contaminates such as iron precipitates (iron sulfate), which may exist or be formed in water, may be removed by filtration of the mixture prior to excitation in the fluorometer. Other methods of eliminating the influence of undesirable contaminants, such as adjusting excitation and emission wavelengths, or changing surfactant additives, have been mentioned above. Another solution is to add a compound which would react with the contaminant, creating a precipitate which could be removed. These and other methods of removing contaminants are known to those skilled in the art. Although biomass will not normally cause an upset with the invention method, it may be desirable to remove such biomass if entrained or adsorbed oil is carried with it.

A mechanical or physical means may be used in the invention method to aid the surfactant in solubilizing the free oil in the water so that it can be measured for fluorescence. The means to aid solubilizing may be a high shear pump, an ultrasonic bath, a static mixer or a high powered, well focused microwave field.

Although there are a number of applications of the invention method, its use as a detector of upsets in treated water streams is a prime interest to the oil industry. In such an application, the use of the additive can be substantially reduced by using the method only when a turbidity meter registers an alarm. At such a time, surfactant would be mixed into the produced water, a fluorescent reading taken, a comparison made, and the turbidity meter alarm confirmed or rejected. The invention method measures oil and is not sensitive to turbidity.

The following examples will further illustrate the novel method of determining the total amount of oil, including dispersed hydrocarbon, in water by the present invention. These examples are given by way of illustration and not as limitations on the scope of the invention. Thus, it should be understood that the steps of the invention method may be varied to achieve similar results within the scope of the invention.

EXAMPLES

In the following examples, a Turner Design Digital Fluorometer Model 10-AU-005 was employed. The fluorometer had a Turner Design flow through cell with clean-out accessory. This converted the fluorometer to an on-line system with valves to shut off a sample stream while the fluorometer was being calibrated. A valve was also included for quick access to the flow cells, facilitating cleaning. For these examples, a long wavelength oil kit supplied by Turner Design was used. The kit contained a near UV lamp, filters No. 7-37, 2A, and 4-96. This combination of lamp and filters resulted in most excitation radiation entering the sample cell at about 365 nm and emission wavelength measurement in the range of 410–550 nm.

In certain cases, such as the measurement of very light or refined oils, shorter excitation and emission wavelengths may be more helpful. One example would be the short wavelength oil kit sold by Turner Design with excitation wavelengths concentrated around 254 nm and emission wavelengths measured mostly around 450 nm. With a short wavelength kit, certain water treating chemicals may have a greater fluorescent effect.

An option for light oils low in aromatic content is to increase the measurement cell size in the fluorometer. Such oils will have a low quantity of chromophores and low fluorescence. Larger flow cells should help to accentuate any fluorescent measurements obtained. Of course, any number of excitation and emission wavelengths are possible and can be deduced by those skilled in the art upon experimentation.

Another option is to use a "falling stream" optical system in conjunction with a fluorometer. With such a system, the fluorometer is modified so that a stream of fluid, perhaps about 3 mm in diameter, passes through the light path. It is desirable to provide constant ventilation around the stream to minimize condensation upon the optics. Such a falling stream design is less likely to have scale buildup or biomass or other contaminant fouling compared to a traditional flow-through design.

But this invention method is not limited to the use of specific fluorometer designs and models. We believe that most any spectrophotometric apparatus may be used that could excite the hydrocarbons and measure their emission radiation within the specified ranges. Examples include such spectrophotometric apparatus such as turbidimeters, UV-visible spectrophotometers, and infrared spectrophotometers.

Surfactants sold by Texaco Chemical Co. under the registered trademark Surfonic ® product line that have been tested are shown below with their descriptions.

TABLE A

| Surfonic ® | HLB[1] | Cloud Point[2] | Structure |
|---|---|---|---|
| L24-3 | 8 | 45 ml in $H_2O$ | C12–C14 synthetic alcohols plus 3 moles of ethylene oxide |
| L24-7 | 11.9 | 50° C. | C12–C14 synthetic alcohols plus 7 moles of ethylene oxide |
| L24-9 | 13 | 75° C. | C12–C14 synthetic alcohols plus 9 moles of ethylene oxide |
| L24-12 | 14.4 | 97° C. | C12–C14 synthetic alcohols plus 12 moles of ethylene oxide |
| L46-7 | 11.6 | 50° C. | C14–C16 synthetic alcohols plus 7 moles of ethylene oxide |
| LF-17 | — | 32° C. | C8–C18 alcohols linear, ethoxylated propoxylated |

[1]HLB is an abbreviation for hydrophilic/lipophilic balance.
[2]Cloud Point is reported in °C. for 45 ml of the surfactant in 1000 ml of $H_2O$ A bath of treated produced water (Treated Water) from the Junction water plant at Kern River, Calif. was held at 60° C. and recirculated through a Turner Design fluorometer containing a flow through cell. When used herein, Treated Water refers to produced water after it has been treated in a mechanically induced gas flotation unit (IGF). Numerous versions of IGF units have been commercialized in the last twenty years for use in the oil patch. Most consist of mechanical aeration cells in series, wherein gas bubbles are generated to contact oil droplets within the water and carry the oil droplets to the surface where they can be skimmed off. At times, polyelectrolytes or surfactants are added to enhance this action. The IGF units employed at Kern River to provide Treated Water for these example experiments normally outflow water having a free oil content of about 1 ppm, by Hach oil in water test, unless an upset in the system occurs, such as a slug of oil.

Samples of this treated produced water were treated with surfactant and oil, and then passed through the funnel portion of the fluorometer. The fluorescent reading numbers are unitless. The more fluorescent material in solution yields a higher fluorescence reading.

A high shear blender was used to mix the surfactants and oil into the water. Mixing was usually 15–30 seconds in duration. These samples were then placed in a water bath at 60° C. to maintain this temperature. The oil was a viscous crude obtained from a Kern River well having about a 17° API gravity, which was not treated with an emulsion breaker or reverse emulsion breaker. The oil and water samples resembled chocolate colored produced water with some floating oil. Either 3 cm³ or 6 cm³ of the chocolate colored water was used in these experiments. As determined by the Hach "Oil-In-Water" method identified above, 3 cm³ in 1 L of Treated Water was equal to 5 mg/L of oil, and 6 cm³ in 1 L of Treated Water was equal to 11 mg/L of oil.

Example 1

The Example 1 tests, which were repeated numerous times, show the lack of significant differences in fluorescent readings when attempting to measure free oil in the Treated Water. Little fluorescent material was detected with free oil mixed into the Treated Water.

TABLE 1

| Sample | Fluorescent Reading | Comments |
|---|---|---|
| Treated Water | 9.22 | |
| Treated Water + oil | 9.65 | 16 cm³ oil added to one liter Treated Water |

Example 2

The solutions of surfactant and oil were mixed vigorously with the Treated Water on a stir plate for 30–60 seconds instead of using a high shear blender. This method is preferred, since foaming is reduced, which can interfere with the fluorescent readings. All of the nonionic surfactants of Table 2, (identified in Table A) were added at a concentration of 0.5% by weight. All of the solutions were measured at 60° C.

TABLE 2

| Sample | Fluorescent Reading | Comments |
|---|---|---|
| Treated Water | 8.95 | |
| Treated Water + L24-3 | 10.1 | Solution was turbid. |
| Treated Water + L24-3 + Oil (6 cm³) | 19.7 | Some of the chemical was floating on top of the water. |
| Treated Water | 9.01 | |
| Treated Water + L24-7 | 9.28 | |
| Treated Water + L24-7 + Oil (6 cm³) | 22.2 | |
| Treated Water | 9.05 | Globules floated on the surface. |
| Treated Water + LF-17 | 11.4 | |
| Treated Water + LF-17 + Oil (6 cm³) | 16.4 | |
| Treated Water | 8.92 | |
| Treated Water + L46-7 | 10.52 | |
| Treated Water + L46-7 + Oil (6 cm³) | 20.7 | |
| Treated Water | 9.0 | |
| Treated Water + L24-9 | 8.78 | |
| Treated Water + L24-9 + Oil (6 cm³) | 17.5 | |
| Treated Water | 9.04 | |
| Treated Water + L24-12 | 8.68 | |
| Treated Water + L24-12 + Oil (6 cm³) | 11.7 | |

The results show that an interaction took place between the surfactant and oil. The L24-7 was the most preferred additive, producing the best response from the instrument. Using similar data with additional data points, a correlation table can be developed to allow a fluorometer reading to be converted into a mg/L number approximately equal to that reached by the Hach Oil-In-Water Test.

Example 3

In these tests, a number of common treating chemicals were mixed into 1 liter of Treated Water at a 50 ppm level along with 0.5% L24-7 by weight. Table 3 indicates that only a small increase in fluorescence occurred. These results and others indicate that the use of many treating chemicals will not significantly affect the fluorescent method of the present invention, particularly since most treating chemicals are used at far lower concentrations of about 1 to 5 ppm. However, this is not a universal truth. Individual treating chemicals should be tested for their effect. All of the solutions were measured at 60° C.

TABLE 3

| Sample | Fluorescent Reading |
|---|---|
| Treated Water | 8.82 |
| Treated Water + RP815 + RP4194 + J301 + DX1559 + L24-7 | 9.65 |

Example 4

A dispersant sold under the trademark Corexit 9527 by Exxon has been used on oil spills in waterways. According to the MSDS sheet, this material is composed of an ether solvent and fatty acid esters. This dispersant falls into the broad class of nonionic surfactants. Table 4 shows the testing of Corexit 9527 as an additive under the invention method. Clearly, the Corexit was ineffective in the invention method to determine free oil-in-water. The dispersant has an orange-amber color which apparently contributes to the fluorescent reading. Such color and increase in fluorescence is probably due to an aromatic or multiple bond structure in the Corexit surfactant. All of the solutions were tested at 60° C.

TABLE 4

| Sample | Fluorescent Reading |
|---|---|
| Treated Water (60° C.) | 6.83 |
| Treated Water (1 liter) + 5 ml Corexit 9527 | 10.8 |
| Treated Water (1 liter) + 5 ml Corexit 9527 + 12 cm³ oil | 10.9 |

Example 5

Fluorescence responds linearly up to certain concentrations of aromatics before quenching of the fluorescent signal begins, reducing the fluorescent reading. This linear relationship was illustrated by the runs of Table 5 where successive amounts of oil where added to the Treated Water containing the additive L24-7. The Hach Oil-In-Water Test yielded the following results.

Treated Water only = 1 ppm
Treated Water + 3 cm³ oil = 5 ppm
Treated Water + 6 cm³ oil = 10.5 ppm A plot of the fluorescent readings of Table 5 versus the oil concentration yields a strong linear relationship.

TABLE 5

| Sampe | Fluorescent Reading |
|---|---|
| Treated Water (20° C.) | 8.97 |
| Treated Water (60° C.) | 7.89 |
| Treated Water + L (5 mL/1 L) + 3 cm³ oil | 13.5 |
| Plus 3 cm³ oil | 18.5 |
| Plus 3 cm³ oil | 23.6 |
| Plus 3 cm³ oil | 29.0 |
| Plus 3 cm³ oil | 33.8 |
| Plus 6 cm³ oil | 42.6 |
| Plus 6 cm³ oil | 52.3 |
| Plus 6 cm³ oil | 60.6 |
| Plus 6 cm³ oil | 68.6 |

Example 6

One of the advantages of determining free oil by the invention method is that biomass does not significantly affect fluorescent readings. Turbidity meters currently employed react to biomass, biasing their results.

A carboy of Treated Water from the Junction water plant was obtained containing a large amount of biomass which can be evenly dispersed in the water by shaking. The Hach Oil-In-Water Test yielded 19 ppm of oil. Table 6 illustrates the lack of effect biomass has on the invention method.

TABLE 6

| Sample | Fluorescent Reading |
|---|---|
| Treated Water outlet (60° C.) | 9.30 |
| Treated Water + biomass | 9.28 |
| Treated Water + biomass + L24-7 (5% by weight) (mix 1 minute at 60° C.) | 8.96 |
| Hold last test sample for 10 minutes at 60° C. | 14.3 |

The contact time for the additive to interact with free oil is seconds, a maximum of one minute. No increase in fluorescence was obtained after a one minute exposure of the biomass to the additive. After 10 minutes, an increased reading occurred due to oil aromatics being released from the biomass. If this biomass is representative of the usual upsets in treated produced water streams, then oil trapped in biomass should not be a problem in the invention method.

Example 7

Oil from the Captain Prospect in the North Sea was tested with an API Gravity of about 16°–18°. A response similar to the previous examples was observed. Treated Water from the Kern River field was used since produced water from the Captain Prospect was not available. This may have resulted in the slightly higher readings observed for oil and Treated Water only.

TABLE 7

| Sample | Fluorescent Reading |
|---|---|
| Treated Water (60° C.) | 8.20 |
| Treated Water (1 liter) + 66 ppm Captain oil (60° C.) | 10.5 |
| Above solution + 5 ml L24-7 | 27.5 |

Example 8

Two light oils were tested from the Gulf Coast area: High Island crude with a 44.7° API gravity and a Lake Salvador crude with a 39.7° API gravity. Since produced water was not available from these locations, Houston, Tex. tap water was used in the Table 8 tests.

TABLE 8

| Sample | Fluorescent Reading |
|---|---|
| Lake to Salvador Oil | |
| Houston tap | 0.0 |
| 1 L Houston tap + 5 ml of L24-9 | 0.067 |
| Above solution + 25 ppm oil | 3.15 |
| 1 L Houston tap + 21 ppm oil | 0.262 |
| High Island | |
| 1 L Houston tap + 36 ppm oil | 0.506 |
| 5 ml L24-9 + 31 ppm oil | 0.899 |

The low aromatic levels of these light oils resulted in a low fluorescence response as predicted. But it is possible to use a larger diameter fluorometer cell to improve sensitivity and allow an increased fluorometer response. A different nonionic additive might also improve the invention method response to these light oils.

Example 9

A series of experiments were conducted to determine the effectiveness of other commercially available surfactants in the invention method. After all the components were added together, the solutions were mixed for 1 minute with a stir bar. Table 9A shows the results. The baseline fluorescent reading was 6.10 at 60° C.

TABLE 9A

| Oil Amount | Additive | Amount | Fluorescent Reading |
|---|---|---|---|
| None | sodium dodecyl sulfate | 5 g | 6.40 |
| 6 cm³/1 L | sodium dodecyl sulfate | 5 g | 7.70 |
| None | Joy ® detergent (new cleaner rinsing) | 5 cm³ | 6.77 |
| 6 cm³/1 L | Joy ® detergent | 5 cm³ | 18.8 |
| None | Witco AOS (40% active) | 12.5 cm³ | 6.48 |
| 6 cm³/1 L | Witco AOS (40% active) | 12.5 cm³ | 8.08 |
| 6 cm³/1 L | Hexadecanesulfonic acid | 5 g | 10.70 |
| None | Stepan Biosoft D-40 (40% active) | 12.5 cm³ | 7.61 |
| 6 cm³/1 L | Stepan Biosoft D-40 (40% active) | 12.5 cm³ | 9.80 |
| None | Cetyltrimethylammonium chloride | 25 cm³ | 6.61 |

TABLE 9A-continued

| Oil Amount | Additive | Amount | Fluorescent Reading |
|---|---|---|---|
| 6 cm³/1 L | Cetyltrimethylammonium chloride | 25 cm³ | 10.1 |
| 6 cm³/1 L | Texaco L24-9 | 5 cm³ | 25.2 |

As can be seen from Table 9A, the most effective additive was L24-9. Joy ® (a registered trademark of Proctor & Gamble) detergent was also effective. We suspect this product contains ethoxylated materials as the contents list nonionic surfactants as a component. The other commercially available compounds tested were not very effective. Witco AOS is a trademark for an alpha olefin sulfonate sold by the Witco Chemical Co. Stepan Biosoft D-40 is a trademark for a linear alkylbenzene sulfonate sold by Stepan Chemical Co. A significant difference in fluorescence is desirable to allow the instrument to sense as much of the free oil as possible for accuracy. Table 9B shows the types of surfactants tested.

TABLE 9B

| Brand Name | Chemical Formula | Type |
|---|---|---|
| Noble | Sodium dodecyl sulfate | Anionic |
| Joy Detergent | — | Anionic, nonionic surfactants, dispensing aid, water, perfume, stabilizing agents |
| Witco AOS | Alkyl C14-C-16) olefin sulfonate | Anionic |
| None | Hexadecanesulfonic acid | Anionic |
| Stepan Biosoft D-40 | Linear alkylbenzene sulfonate | Anionic |
| None | Cetyltrimethylammonium | Cationic |

The Witco AOS was usable despite its aromaticity since the instrument was set up to observe higher emission wavelengths. If lower excitation and emission wavelengths are used then this type of surfactant would be unacceptable since it would dominate the fluorescent reading. The aromatic additives are also undesirable since they are more difficult to biodegrade.

Example 10

A series of experiments were conducted to determine if other commercially available additives are as effective as Texaco's nonionic ethoxylates with the free oil in water detecting method. The following table shows the results with oil (39.7° API) from the Gulf Coast Lake Salvador field. The procedure consisted of adding the different additives at a 0.5% amount by weight to Houston tap water at 20° C., since no produced water was available from this area. The Lake Salvador oil was added first at a 50 ppm level, followed by the additive. The solution was then mixed for 1 minute with a stir bar.

TABLE 10

| Oil Amount | Additive | Amount | Fluorescent[1] Reading |
|---|---|---|---|
| 0.0495 g | Sodium dodecyl sulfate | 5 g | 1.04 |
| 0.0523 g | Witco AOS (40% active) | 12.5 cm³ | 1.13 |
| 0.0508 g | Hexadecanesulfonic acid | 5 g | 0.54 |
| None | Stepan Biosoft D-40 (40% active) | 12.5 cm³ | 0.74 |
| 0.0476 g | Stepan Biosoft D-40 (40% active) | 12.5 cm³ | 1.92 |

TABLE 10-continued

| Oil Amount | Additive | Amount | Fluorescent[1] Reading |
|---|---|---|---|
| 0.0478 g | Cetyltrimethylammonium chloride | 25 cm³ | 0.99 |
| None | Texaco L24-9 | 5 cm³ | 0.07 |
| 0.0563 g | Texaco L24-9 | 5 cm³ | 2.09 |
| None | Exxon Corexit | 5 cm³ | 4.26 |
| 0.0531 g | Exxon Corexit | 5 cm³ | 4.81 |

[1]Baseline fluorescent reading 0.0 at 20° C.

These results show that the most effective surfactant additive is the nonionic L24-9. Since the additive must contact the dispersed free oil and interact within seconds, the larger the fluorometer response is to the free oil, the more accurate the reading is on the amount of free oil present.

Example 11

A series of experiments were conducted to determine if commercially available oil-soluble surfactants from the Stepan Chemical Co. are effective with the invention free oil monitoring system. The procedure consisted of using the Stepan additives at a 0.5% level in one liter of Treated Water. The components were added together and mixed for 1 minute with a stir bar. Tested additives are sold by the Stepan Chemical Co. under the trademarks: Petrostep B-120 (alkylaryl sulfonate), Petrostep B-100 (alkylaryl sulfonate), and Petrostep H-62 (alkylbenzene sulfonic acid).

TABLE 11

| Oil Amount | Additive | Amount | Fluorescent 1 Reading |
|---|---|---|---|
| None | Petrostep B-120 (52% active) | 9.6 ml | 84 |
| None | Petrostep B-100 (91% active) | 5.5 ml | 27.2 |
| None | Petrostep H-62 (84% active) | 15.3 ml | 15.3 |

1 Baseline fluorescent reading of 6.7 at 60° C.

As can be seen, these oil soluble surfactants by themselves yield too high a fluorescent reading to be effective with the instant free oil detection method.

Example 12

A series of experiments were conducted to determine if other commercially available additives from Stepan are effective. The following table shows the results with oily produced water from the Kern River field which can be characterized as a heavy naphthenic crude. The procedure consisted of using the additives at a 0.5% level in one liter of Kern River Treated Water. After all the components were added together, the solution was mixed for 1 minute with a stir bar.

The tested additives were a water soluble detergent and two amine oxides sold by Stepan Chemical Co. under the trademarks:

Biosoft D-62 (58% active linear sodium alkylbenzene sulfonate)

Ammonyx DMCD-40 (40% active lauramine oxide), and

Ammonyx Co. (30% active cetamine oxide).

TABLE 12

| Oil Amount | Additive | Amount, cm³ | Fluorescent[1] Reading |
|---|---|---|---|
| 5 cm³/L | Texaco L24-9 | 5 | 20.5 |
| None | Biosoft D-62 | 8.6 | 10.0 |
| 5 cm³/L | Biosoft D-62 | 8.6 | 10.5 |
| None | DMCD-40 | 12.5 | 7.5 |
| 5 cm³/L | DMCD-40 | 12.5 | 11.0 |

TABLE 12-continued

| Oil Amount | Additive | Amount, cm³ | Fluorescent[1] Reading |
|---|---|---|---|
| None | CO | 16.6 | 7.38 |
| 5 cm³/L | CO | 16.6 | 13.7 |

[1]Baseline fluorescent reading of 7.97 at 60° C.

The L24-9 is the most effective additive compared to these Stepan surfactants. The Ammonyx CO does produce a good response to the presence of oil. The other surfactants were not effective.

Example 13

Iron is often a component in oilfield water producing a yellow colored solution. To show that iron does not have a significant effect on the invention method, the following experiment was done.

Iron(II) chloride heptahydrate (1 gram) was dissolved in 1 liter of Treated Water from the Kern River field. A large amount of green solid formed (iron sulfate), and this solution was passed through the instrument. The solid was then removed by filtration, yielding a yellow solution which was passed through the instrument. The results are shown below in Table 13.

TABLE 13

| Sample | Fluorescent Reading |
|---|---|
| Treated Water 60° C. | 6.40 |
| Treated Water (1 liter) + iron(II) chloride with solid | 4.80 |
| Filtered solution | 6.18 |

No increase in fluorescence was observed due to the yellow color of iron. The low reading of 4.80 was due to blockage of light through the cell by the high solids. In a preferred invention method location, the amount of iron solids produced in this experiment would not be encountered.

Example 14

These tests were conducted to determine if mixing a light oil (Lake Salvador—39.70 API) with the additive followed by addition to Houston tap water yields a different result versus adding the free oil to the water prior to the additive. The results are shown below in Table 14.

TABLE 14

| Oil Amount | Additive | Amount, cm³ | Fluorescent[1] Reading |
|---|---|---|---|
| None | L24-9 | 5 | 0.07 |
| 0.0563 g | L24-9 + oil + Houston tap | 5 | 8.02 |
| 0.0563 g | L-24-9 + water + oil | 5 | 2.09 |

[1]Baseline fluorescent reading of Houston tap 0.0 at 20° C.

The results indicate there is a difference when the additive comes in direct contact with this light oil prior to water addition than when water is present before the additive. The water apparently makes it more difficult for the additive to solubilize this light oil. It is believed that better mixing and longer contact times will improve the fluorescent readings with light oils which generally have less of the components which produce significant fluorometer readings.

Example 15

A set of experiments were performed using produced water contaminated with free oil with and without a surfactant of L24-9. The solutions were studied using a ratio turbidimeter and a particle size analyzer. A summary of the data collected when testing a solution contaminated with free oil and the same solution after adding a given volume of a surfactant is shown in Table 15.

These experiments suggest a theory for the operation of the invention method. It is believed that selected surfactants are able to substantially reduce oil droplet size and disperse the oil more uniformly within the water so that the oil may be more easily excited to fluorescence. It is believed that the larger oil droplets and their surface tension effects interfere with fluorescence measurement of oil content.

TABLE 15

| Solution | Turbidity (NTU) | Particle Population (counts) |
|---|---|---|
| Filtered Produced Water & oil | 14.8 | 55% above 3 micron median of 3.62 micron |
| Filtered Produced water & oil & surfactant (L24-9) | 7.3 | 14.1% above 3 micron median of 1.68 micron |

The data indicates that the surfactant reacted with the oil droplets reducing their size and shifting the population size distribution. This effect is further confirmed by comparing the median population size of both solutions. The solution with the surfactant shows a median size of 1.68 micron while the other solution exhibits a median of 3.62 micron.

A decrease in the size of the oil droplets by adding a surfactant is also supported by analyzing the turbidity data. A substantial decrease in turbidity is observed in the solution containing the surfactant since the newly formed, small size droplets will scatter the incident light less efficiently. By changing the size of the oil droplets we will undoubtedly change the spectrophotometric properties of a solution.

Many other variations and modifications may be made in the concepts described above by those skilled in the art without departing from the concept of the present invention. Accordingly, it should be clearly understood that the concepts disclosed in the description are illustrative only and are not intended as limitations on the scope of the invention.

What is claimed:

1. A method to determine the amount of hydrocarbon, including dispersed oil, in water at ppm levels, which comprises:

mixing surfactant with water which may contain dispersed hydrocarbon, said surfactant comprising a non-aromatic linear alcohol having about 10 to about 15 carbon atoms in the alkyl chain, about 3 to about 10 groups of ethylene oxide, and able to solubilize into water the particular oil being tested for;

exciting the mixture of surfactant and water in a fluorometer at an excitation wavelength between about 200 and about 400 nanometers;

determining the amount of dispersed oil in the water by comparing the emission fluorescence of said mixture to previous correlations, said previous correlations drawn between known amounts of oil-in-water and their emission fluorescence under similar conditions.

2. The method of claim 1, wherein the emission fluorescence is measured between about 250 and about 600 nanometers.

3. The method of claim 1, said surfactant is a relatively low foaming surfactant.

4. The method of claim 1, wherein about 0.1% to about 3% by weight of said surfactant is mixed with the water which may contain oil.

5. The method of claim 1, wherein about 0.3% to about 0.7% by weight of said surfactant is mixed with the water which may contain oil.

6. The method of claim 1, further comprising using a mechanical means to aid said surfactant in solubilizing the free oil in the water.

7. The method of claim 6, wherein the mechanical means used to aid solubilizing is a high shear pump, ultrasonic bath, static mixer or a microwave field.

8. The method of claim 1, wherein the fluorometer is a flowing stream fluorometer.

9. A method to determine the amount of dispersed oil in a produced water stream at ppm levels, which comprises:

mixing about 0.3% to about 0.7% by weight of a non-aromatic surfactant with a produced water stream which may contain dispersed oil, said surfactant being a linear alcohol having about 10 to about 15 carbon atoms in an alkyl chain, about 3 to about 10 groups of ethylene oxide, and able to solubilize into water the oil being tested for;

exciting the mixture of surfactant and water in a fluorometer at an excitation wavelength between about 200 and about 400 nanometers;

determining the amount of dispersed oil in the water by comparing the emission fluorescence between about 250 and about 600 nanometers of said mixture to previous correlations, said previous correlations drawn between known amounts of oil in a produced water stream and their emission fluorescence under similar conditions.

* * * * *